US010470910B2

(12) United States Patent
Folan et al.

(10) Patent No.: US 10,470,910 B2
(45) Date of Patent: Nov. 12, 2019

(54) MULTIPLE STENT SYSTEM FOR GI TRACT DRAINAGE

(71) Applicant: BOSTON SCIENTIFIC SCIMED, INC., Maple Grove, MN (US)

(72) Inventors: Martyn G. Folan, Loughrea (IE); Geraldine A. Toner, Raphoe (IE); Matthew Montague, Galway (IE)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 368 days.

(21) Appl. No.: 15/398,267

(22) Filed: Jan. 4, 2017

(65) Prior Publication Data

US 2017/0189217 A1 Jul. 6, 2017

Related U.S. Application Data

(60) Provisional application No. 62/274,994, filed on Jan. 5, 2016.

(51) Int. Cl.
*A61F 2/852* (2013.01)
*A61F 5/00* (2006.01)
*A61F 2/82* (2013.01)

(52) U.S. Cl.
CPC ............ *A61F 5/0076* (2013.01); *A61F 2/852* (2013.01); *A61F 2002/823* (2013.01); *A61F 2002/826* (2013.01); *A61F 2230/0019* (2013.01); *A61F 2230/0023* (2013.01); *A61F 2230/0069* (2013.01); *A61F 2250/006* (2013.01); *A61M 2205/04* (2013.01); *A61M 2210/1042* (2013.01)

(58) Field of Classification Search
CPC ........ A61F 2002/826; A61F 2230/0019; A61F 2230/0023; A61F 2230/0069; A61F 2/852; A61F 5/0076; A61M 2205/04; A61M 2210/1042; A61M 27/00
See application file for complete search history.

(56) References Cited

U.S. PATENT DOCUMENTS

| | | | |
|---|---|---|---|
| 8,652,083 B2 | 2/2014 | Weitzner et al. | |
| 2002/0179166 A1 | 12/2002 | Houston et al. | |
| 2007/0282453 A1 | 12/2007 | Weitzner et al. | |
| 2010/0256731 A1 | 10/2010 | Mangiardi | |
| 2011/0022151 A1* | 1/2011 | Shin | A61F 2/04 623/1.11 |
| 2012/0136430 A1* | 5/2012 | Sochman | A61F 2/2418 623/1.23 |
| 2014/0243992 A1 | 8/2014 | Walsh et al. | |
| 2014/0257466 A1* | 9/2014 | Board | A61F 2/2403 623/2.11 |

* cited by examiner

*Primary Examiner* — Kai H Weng
(74) *Attorney, Agent, or Firm* — Seager, Tufte & Wickhem, LLP

(57) ABSTRACT

A gastrointestinal assembly may be deployed within a patient's gastrointestinal tract in order to facilitate drainage of an abscess. The gastrointestinal assembly may include an outer stent and an inner stent disposed within the outer stent. The inner stent divides a volume within the outer stent into a primary passageway through which nutritional contents may pass and a secondary passageway protected from nutritional contents and configured to accommodate a passive drainage system for draining the abscess.

19 Claims, 16 Drawing Sheets ial Patent
MULTIPLE STENT SYSTEM FOR GI TRACT DRAINAGE

CROSS-REFERENCE TO RELATED APPLICATIONS

This application claims priority to U.S. Provisional Patent Application Ser. No. 62/274,994, filed on Jan. 5, 2016, the contents of which are fully incorporated herein by reference.

TECHNICAL FIELD

The disclosure is directed to devices for facilitating drainage of a gastrointestinal wound such as an abscess. More particularly, the disclosure is directed to a multiple stent system for facilitating drainage of an abscess.

BACKGROUND

Wounds may develop within the gastrointestinal system for a variety of reasons. For example, bariatric surgical procedures create staple lines that may be prone to leakage. In some cases, an abscess may develop along a staple line. In some instances, passive drainage, in which a drain tube is inserted into the abscess in an attempt to drain the abscess and thus promote healing of the abscess, has been used. However, passive drainage is not always as effective as may be desired. In some cases, active drainage, in which a source of vacuum is fluidly coupled with the drain tube, has been used. As will be appreciated, this may require an external source of vacuum. Of the known medical devices and methods, each has certain advantages and disadvantages. There is an ongoing need to provide alternative medical devices as well as alternative methods for manufacturing and using medical devices.

SUMMARY

The disclosure is directed to several alternative designs, materials and methods of manufacturing medical device structures and assemblies, and uses thereof.

A gastrointestinal assembly for facilitating drainage of an abscess is disclosed. The gastrointestinal assembly is configured to be deployed within a patient's gastrointestinal tract proximate the abscess. The assembly includes an outer stent and an inner stent disposed within the outer stent. The outer stent has an expanded configuration in which an outer surface of the outer stent engages the patient's gastrointestinal tract. The outer stent has an inner surface defining a volume within the outer stent. The inner stent has an expanded configuration in which the inner stent divides the volume into a primary passageway through which nutritional contents may pass and a secondary passageway protected from nutritional contents and configured to accommodate a passive drainage system for draining the abscess.

Alternatively or additionally to any of the embodiments above, the outer stent has a cylindrical profile and the inner stent has a non-cylindrical lower portion defining the secondary passageway between the inner stent and the outer stent, and the inner stent has a flared upper portion that is configured to seal against the cylindrical profile of the outer stent.

Alternatively or additionally to any of the embodiments above, the inner stent includes an expandable framework defining the non-cylindrical portion and the flared upper portion and a polymeric covering disposed over at least part of the expandable framework.

Alternatively or additionally to any of the embodiments above, the non-cylindrical lower portion of the inner stent has a polygonal cross-sectional profile.

Alternatively or additionally to any of the embodiments above, the non-cylindrical lower portion of the inner stent has a triangular cross-sectional profile.

Alternatively or additionally to any of the embodiments above, the non-cylindrical lower portion of the inner stent has a rectilinear cross-sectional profile.

Alternatively or additionally to any of the embodiments above, the gastrointestinal assembly further comprises a drainage catheter having a first portion extending through a fistula of the abscess and into the abscess, the drainage catheter having a second portion extending downwardly from the abscess through the secondary passageway.

Alternatively or additionally to any of the embodiments above, the drainage catheter extends through a wall of the outer stent.

A gastrointestinal drainage assembly for facilitating drainage of an abscess is disclosed. The gastrointestinal assembly is configured to be deployed within a patient's gastrointestinal tract proximate the abscess. The assembly includes an outer expandable framework and an inner expandable framework. The outer expandable framework is configured to engage the patient's gastrointestinal tract when in its expanded configuration. The outer expandable framework has a cylindrical profile. The inner expandable framework is disposed within the outer expandable framework and in contact with the outer expandable framework when the inner expandable framework is in its expanded configuration. The inner expandable framework has a non-cylindrical lower portion that defines a nutritional content pathway through the inner expandable framework and one or more drainage pathways disposed between the inner expandable framework and the outer expandable framework. The inner expandable framework has a flared upper portion that engages the outer expandable framework and seals off an upper end of the one or more drainage pathways.

Alternatively or additionally to any of the embodiments above, the gastrointestinal drainage assembly further comprises a drainage catheter having a first portion extending into the abscess and a second portion extending downwardly from the abscess through the one of the one or more drainage pathways.

Alternatively or additionally to any of the embodiments above, the inner expandable framework contacts the outer expandable framework along one or more contact lines, and the inner expandable framework deforms the outer expandable framework in an outward direction along the one or more contact lines in order to anchor the gastrointestinal drainage assembly in position within the gastrointestinal tract.

Alternatively or additionally to any of the embodiments above, the gastrointestinal drainage assembly further comprises a polymeric covering disposed over at least a portion of the inner expandable framework.

Alternatively or additionally to any of the embodiments above, the gastrointestinal drainage assembly further comprises a polymeric covering disposed over at least a portion of the outer expandable framework.

Alternatively or additionally to any of the embodiments above, the non-cylindrical lower portion of the inner expandable framework has a polygonal cross-sectional profile.

Alternatively or additionally to any of the embodiments above, the non-cylindrical lower portion of the inner expandable framework has a triangular cross-sectional profile.

Alternatively or additionally to any of the embodiments above, the non-cylindrical lower portion of the inner expandable framework has a rectilinear cross-sectional profile.

A method of facilitating drainage of an abscess proximate a patient's gastrointestinal tract is disclosed. The method includes advancing an outer stent into position proximate the abscess and expanding the outer stent such that the outer stent makes substantial contact with the gastrointestinal tract. A first end of a drainage catheter is extended through a side wall of the outer stent and into the abscess. The drainage catheter has a length sufficient to permit a second end of the drainage catheter to extend distally from the abscess. An inner stent is advanced into the expanded outer stent and expanded. The expanded inner stent defines a primary passageway through which nutritional contents may pass and a secondary passageway through which the drainage catheter extends. The inner stent has a flared proximal end that seals the proximal end of the secondary passageway to keep nutritional contents out of the secondary passageway.

Alternatively or additionally to any of the embodiments above, the outer stent has a cylindrical profile when expanded and the inner stent, when expanded, has a non-cylindrical lower portion defining the secondary passageway between the inner stent and the outer stent.

Alternatively or additionally to any of the embodiments above, expanding the inner stent causes the inner stent to contact the outer stent along one or more contact lines, and the inner stent deforms the outer stent in an outward direction along the one or more contact lines in order to anchor the gastrointestinal drainage assembly in position within the gastrointestinal tract.

Alternatively or additionally to any of the embodiments above, the method further comprises a subsequent step of removing the inner stent, the outer stent and the drainage catheter once the abscess has healed.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE FIGURES

The aspects of the disclosure may be further understood in consideration of the following detailed description of various embodiments in connection with the accompanying drawings, in which.

Figure 1:
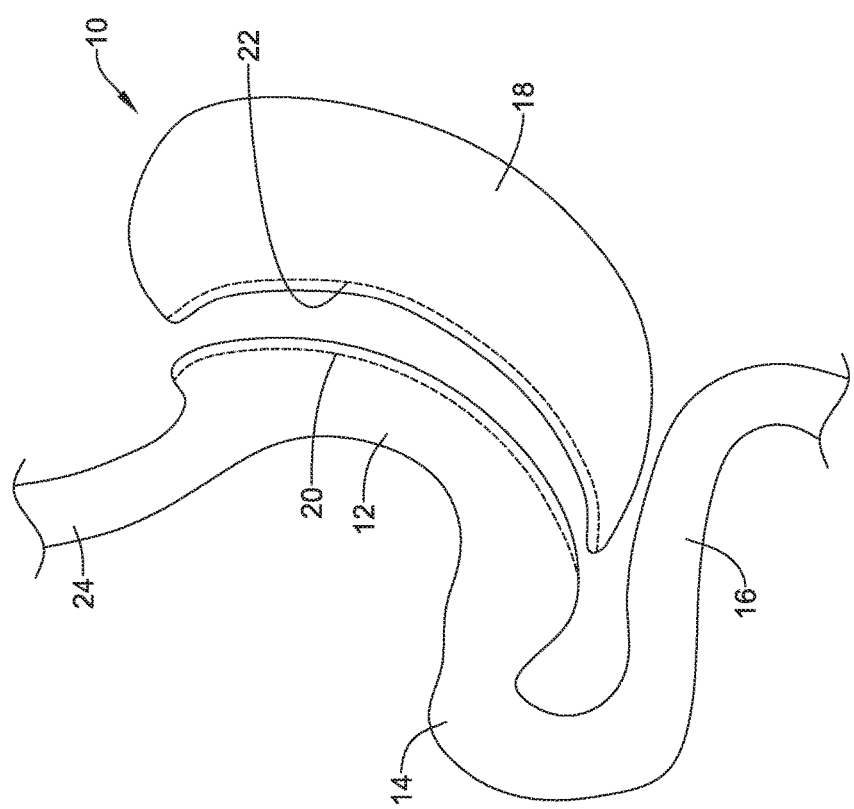
FIG. 1 is a schematic illustration of a gastric sleeve procedure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

There are a number of conditions, diseases and surgical interventions that may result in wounds such as an abscess within the gastrointestinal tract. In many cases, a surgical intervention may create a staple line or suture line within a portion of the gastrointestinal tract. An illustrative but non-limiting example of such a surgical intervention is bariatric surgery. In bariatric surgery, which may be performed as an open surgery or more commonly as a laproscopic surgery, an obese patient's stomach is made substantially smaller. As a result, the patient may be able to lose weight, particularly if they follow corresponding dietary restrictions. There are several common bariatric techniques.

FIG. 1 illustrates the results of a procedure known as sleeve gastrectomy, in which a large portion of a patient's stomach 10 is cut away. As a result, a relatively small attached portion 12 of the patient's stomach 10 remains fluidly coupled through the pylorous 14 with the small intestine 16. As can be seen in FIG. 1, a relatively large resected portion 18 of the patient's stomach 10 is resected, or cut away from the attached portion 12 of the patient's stomach 10 that remains as part of the patient's effective gastrointestinal tract and extends from the esophagus 24 to the small intestine 16 It will be appreciated that as a result of the resection, a large staple line 20 is formed along one side of the small portion 12 of the patient's stomach 10. A corresponding long staple line 22 is formed along one side of the resected portion 16 of the patient's stomach 10.

Figure 2:
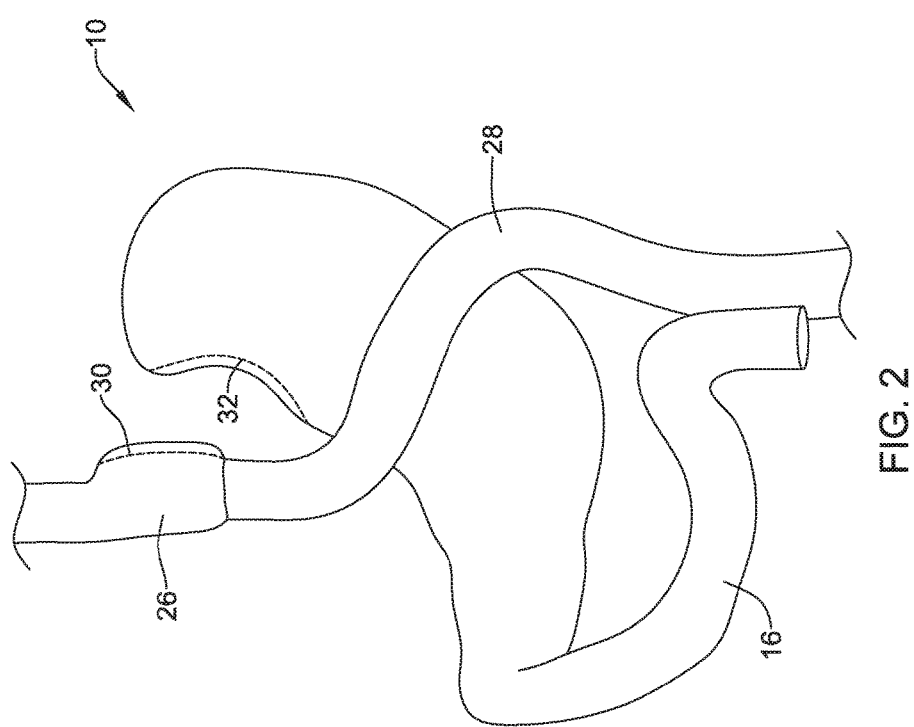
FIG. 2 is a schematic illustration of a Roux-en-Y procedure.

FIG. 2 illustrates the Roux-en-Y gastric bypass procedure in which an even larger portion of the patient's stomach 10 is resected and a portion of the small intestine 16 is also bypassed. In this procedure, a pouch 26 is formed from the very uppermost portion of the stomach 10 and is secured to the Roux limb 28, which is a portion of the small intestine 16 that is secured to the pouch 26. It will be appreciated that as a result of the resection, a staple line 30 is formed along one side of the pouch 26. A corresponding staple line 32 is formed along one side of the stomach 10.

It will be appreciated that leaks may occur along these staple lines, including the staple line 20 and the staple line 30. As a result, in some cases a pus-filled abscess may form adjacent the staple line 20 and/or the staple line 30. In some cases, it can be beneficial to place an esophageal stent, which in some cases may be a covered stent, proximate the wound in order to help seal off the leak, protect the wound from harsh stomach acids and keep nutritional contents such as food and beverages away from the wound. In some cases, it can be beneficial to also provide a way to drain the abscess in order to facilitate healing. While leaks may occur along the staple line 22 and/or the staple line 32, it will be appreciated that this disclosure is directed to treating wounds that may be reached from inside the remaining gastrointestinal tract.

Figure 3:
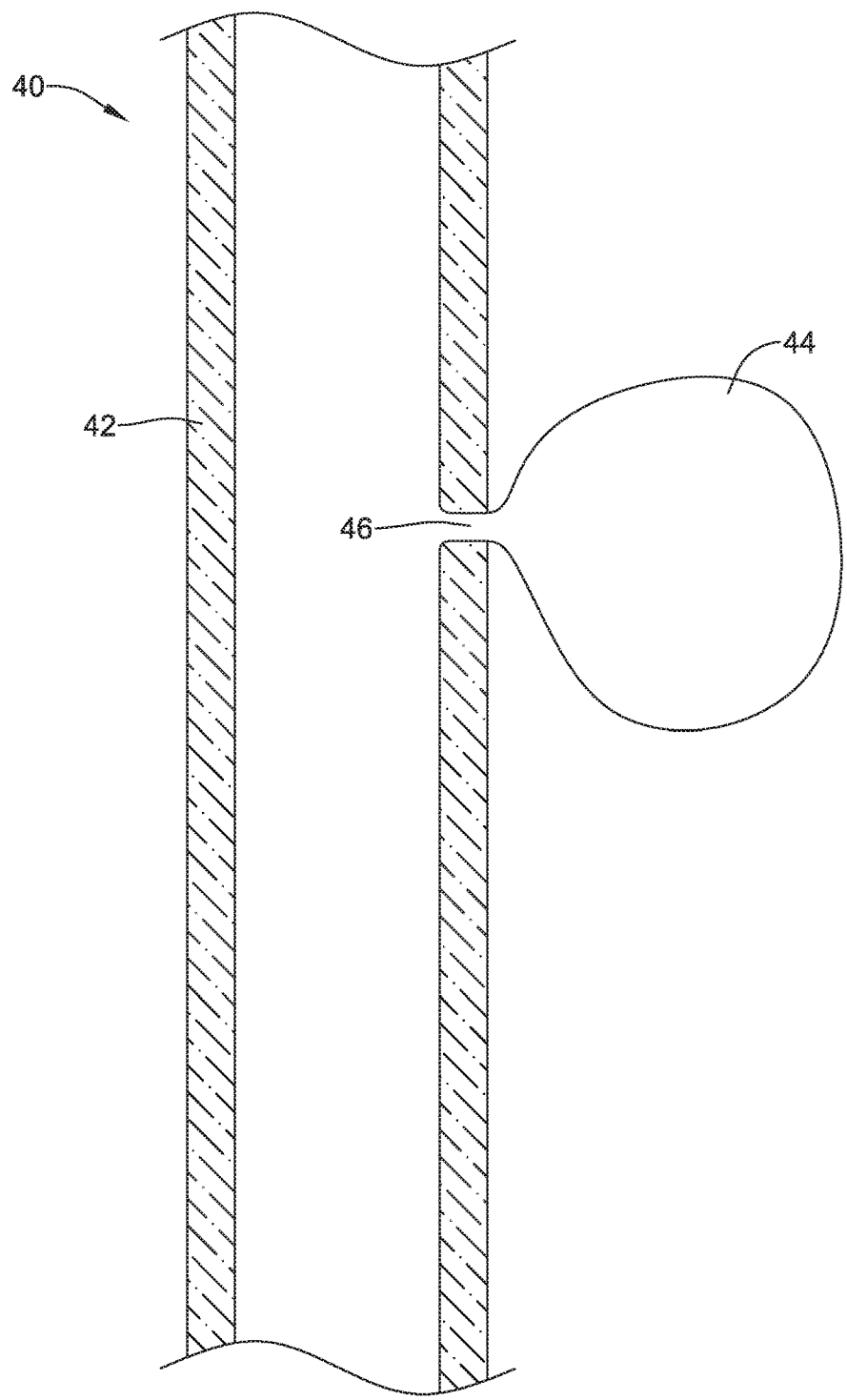
FIG. 3 is a schematic illustration of a portion of a patient's gastrointestinal tract.

FIG. 3 provides a schematic view of a portion of a gastrointestinal tract 40. In some cases, the illustrated portion of the gastrointestinal tract 40 may for example represent part of the patient's esophagus. In some cases, the illustrated portion of the gastrointestinal tract 40 may instead represent a portion of the gastrointestinal tract that has been altered by surgery, such as by one of the bariatric procedures referenced in FIGS. 1 and 2. The gastrointestinal tract 40 includes walls 42 that may be native, undisturbed tissue or that may represent stapled tissue such as would be found for example along the staple line 20 and/or the staple line 30. An abscess 44 may extend from a fistula 46 that passes through the wall 42. The abscess 44 may be filled with pus or other body fluid. It will be appreciated that the abscess 44 is shown schematically.

Figure 4:
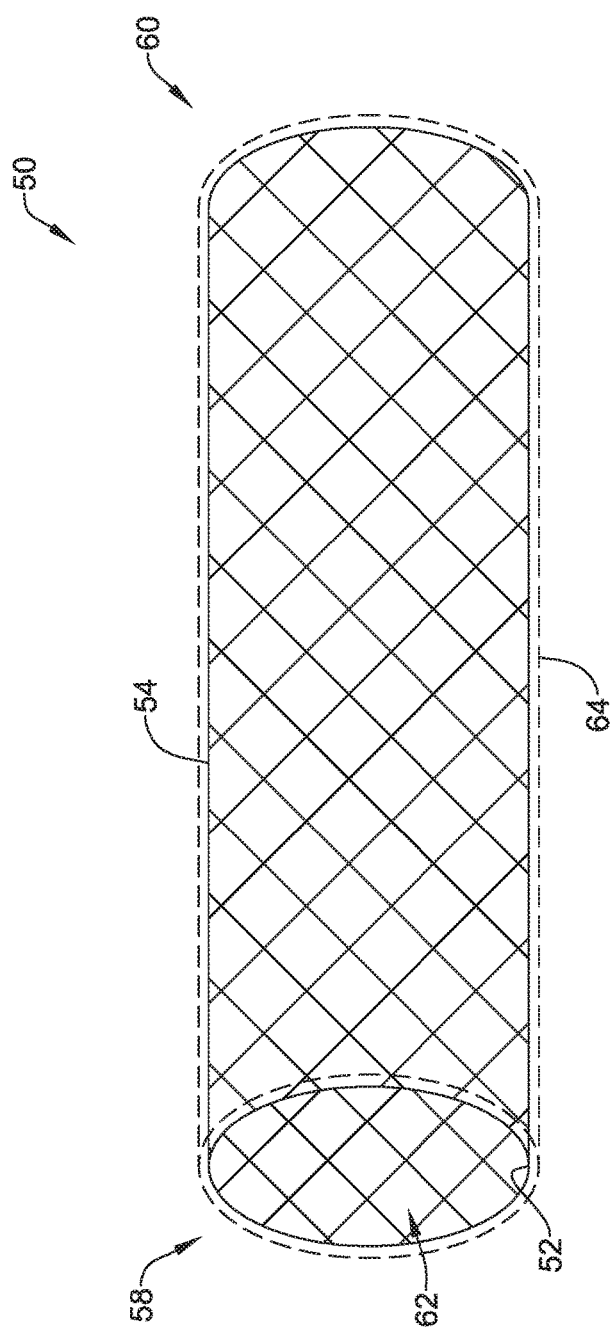
FIG. 4 is a perspective view of an outer stent in accordance with an embodiment of the disclosure.
Figure 5:
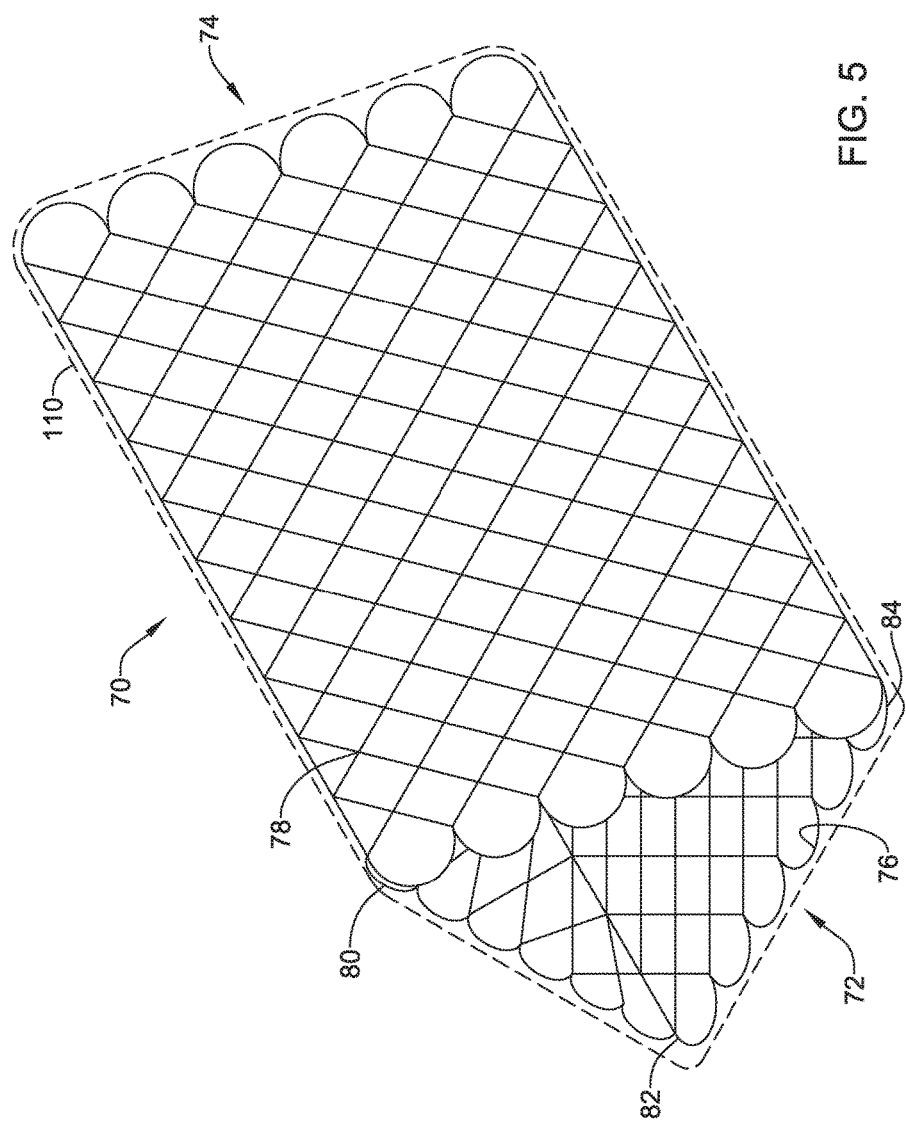
FIG. 5 is a perspective view of an inner stent having a triangular cross-sectional profile in accordance with an embodiment of the disclosure.
Figure 6:
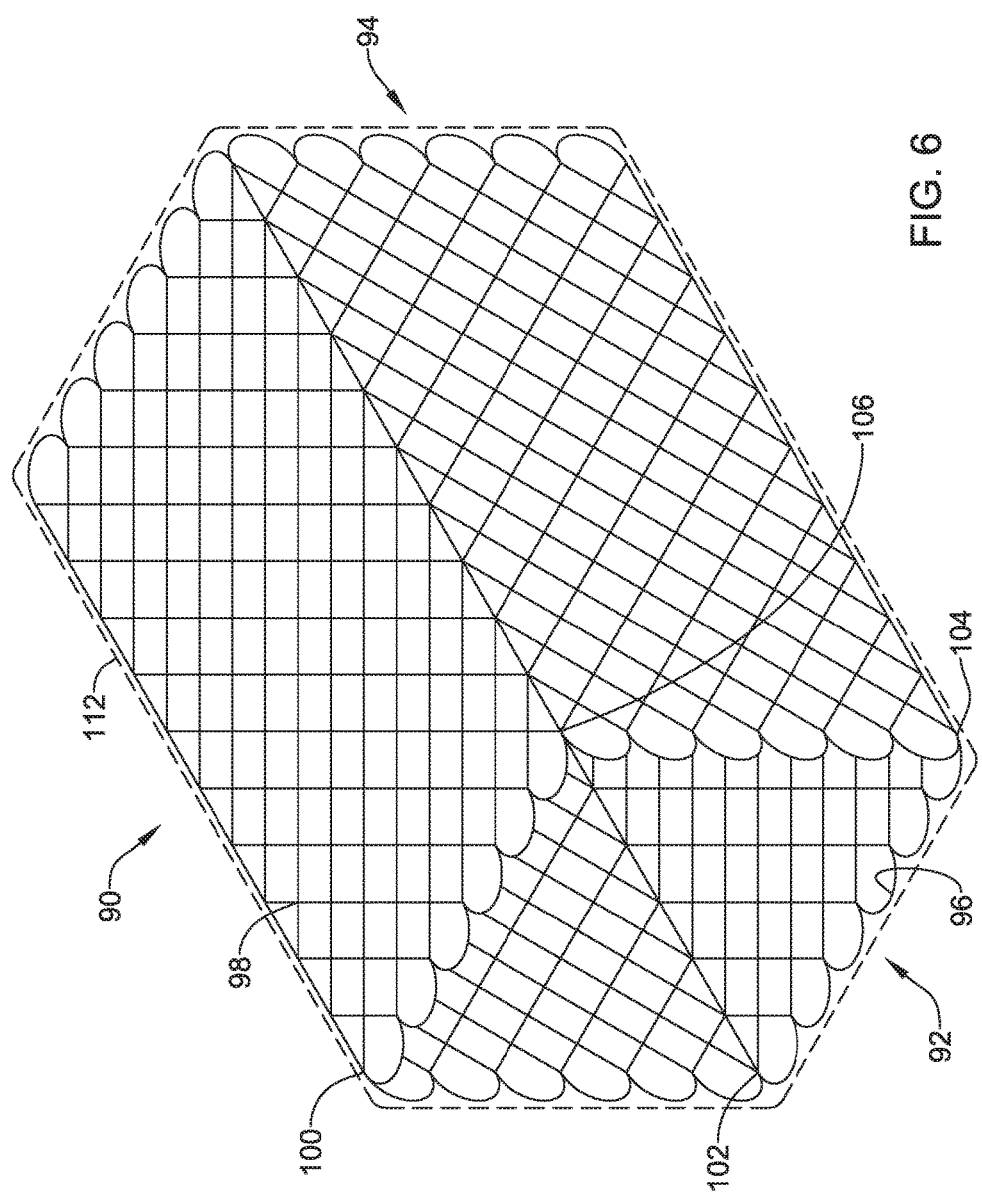
FIG. 6 is a perspective view of an inner stent having a rectilinear cross-sectional profile in accordance with an embodiment of the disclosure.

In some embodiments, a gastrointestinal assembly may be placed within the gastrointestinal tract 40 in order to help heal a wound such as the abscess 44. FIG. 4 provides a view of an exemplary outer stent while FIGS. 5 and 6 provide illustrative but non-limiting examples of inner stents that may be deployed within the outer stent. FIG. 4 illustrates an outer stent 50 having an inner surface 52 and an outer surface 54. The outer stent 50 is expandable between a compressed configuration for delivery and an expanded configuration in which the outer surface 54 may engage the wall 42 of the gastrointestinal tract 40. It will be appreciated that individual patients will have unique gastrointestinal dimensions, and thus the outer stent 50 may be provided having dimensions to accommodate a particular patient. The outer stent 50 extends from a proximal end 58 to a distal end 60, and the inner surface 52 defines a volume or lumen 62 that extends through the outer stent 50 form the proximal end 58 to the distal end 60. In some instances, the outer stent 50 may be considered as being or including an expandable framework. In some cases the outer stent 50 may, for example, be a braided stent, a woven stent or a laser-cut stent. In some cases, the outer stent 50 may include a polymeric covering or coating 64 (shown in phantom) extending over at least part of, or the entire expandable framework, forming a fully or partially covered stent. In some instances, the outer stent 50 may not include the polymeric covering or coating 64. The outer stent 50 may be considered as having a cylindrical profile, i.e., a circular cross-sectional shape taken perpendicular to a central longitudinal axis of the outer stent 50.

In some instances, the outer stent 50 may be used in combination with an inner stent having a non-cylindrical profile. In some cases, for example, an inner stent may have a polygonal cross-sectional profile, defined by a plurality of straight sides converging at a plurality of apices or corners. In some instances, an inner stent may have a triangular cross-sectional profile having three sides and three apices or corners. In some cases, an inner stent may have a rectilinear cross-sectional profile having four sides and four apices or corners. In other instances, the inner stent may have another polygonal profile or cross-sectional shape, such as pentagonal (5 sides and 5 apices/corners), octagonal (8 sides and 8 apices/corners), etc. Thus, embodiments of the inner stent may have three or more sides, such as straight sides, converging at three or more apices or corners.

FIG. 5 illustrates an inner stent 70 extending from a proximal end 72 to a distal end 74. As can be seen, the inner stent 70 has an inner surface 76, an outer surface 78 and a triangular cross-sectional profile, providing a triangular lumen extending through the inner stent 70. In some instances, the inner stent 70 may be considered as being or including an expandable framework. In some cases the inner stent 70 may, for example, be a braided stent, a woven stent or a laser-cut stent. In some cases, the inner stent 70 may include a polymeric covering or coating 110 (shown in phantom) extending over at least part of, or the entire expandable framework, forming a fully or partially covered stent. In some instances, the inner stent 70 may not include the polymeric covering or coating 110.

While illustrated as having a cross-sectional profile that is approximately an equilateral triangle (three equal sides), it will be appreciated that the inner stent 70 may have three sides (in cross-section) that are not all the same length. By virtue of having a triangular profile, it will be noted that the inner stent 70 defines, in cross-section, three corners 80, 82 and 84 that may be considered as forming contact lines where the inner stent 70 may come into contact with an inner surface of the outer stent 50, as will be shown in a subsequent drawing. Thus, the outer stent 50 may circumscribe the inner stent 70, with the apices or corners of the inner stent 70 positioned at the circumference of the outer stent 50.

FIG. 6 illustrates an inner stent 90 extending from a proximal end 92 to a distal end 94. As can be seen, the inner stent 90 has an inner surface 96 and an outer surface 98. The inner stent 90 has a rectilinear cross-sectional profile, providing a rectangular lumen extending through the inner stent 90. As used herein, rectangular and rectilinear profiles or configurations include square cross-sectional profiles or configurations. In other instances, the inner stent 90 may include four sides converging at four apices or corners, forming a parallelogram, trapezoid, diamond, or rhombus cross-sectional profile or configuration. In some instances, the inner stent 90 may be considered as being or including an expandable framework. In some cases the inner stent 90 may, for example, be a braided stent, a woven stent or a laser-cut stent. In some cases, the inner stent 90 may include a polymeric covering or coating 112 (shown in phantom) extending over at least part of, or the entire expandable framework, forming a fully or partially covered stent. In some instances, the inner stent 90 may not include the polymeric covering or coating 112.

As illustrated, the inner stent 90 has a square cross-sectional profile in which each of the four sides (in cross-section) are equal or roughly equal in length. In some embodiments, the inner stent 90 may instead have a rectangular profile, having two relatively shorter sides (in cross-section) and two relatively longer sides (in cross-section). By virtue of having a rectilinear profile, it will be noted that the inner stent 90 defines, in cross-section, four corners 100, 102, 104 and 106 that may be considered as forming contact lines where the inner stent 90 may come into contact with an inner surface of the outer stent 50, as will be shown in a subsequent drawing. Thus, the outer stent 50 may circumscribe the inner stent 90, with the apices or corners of the inner stent 90 positioned at the circumference of the outer stent 50.

The inner stent 70 and the inner stent 90 are merely two examples of stents having non-cylindrical profiles that may be used in combination with the outer stent 50 in treating gastrointestinal wounds such as the abscess 44 (FIG. 3). Other shapes may be utilized in forming the inner stent, such as the inner stent 70, 90. In some cases, the outer stent 50 may have a non-cylindrical profile, particularly if useful in conforming to the shape of the gastrointestinal tract 40 (FIG. 3). In some embodiments, the inner stent 70, 90 has a cross-sectional profile that is different from a cross-sectional profile of the outer stent 50. As a result, the inner stent 70, 90 and the outer stent 50 cooperate to form in combination a pathway for food and other nutritional content as well as forming one or more drainage pathways that may provide space for drainage catheter(s).

Figure 7:
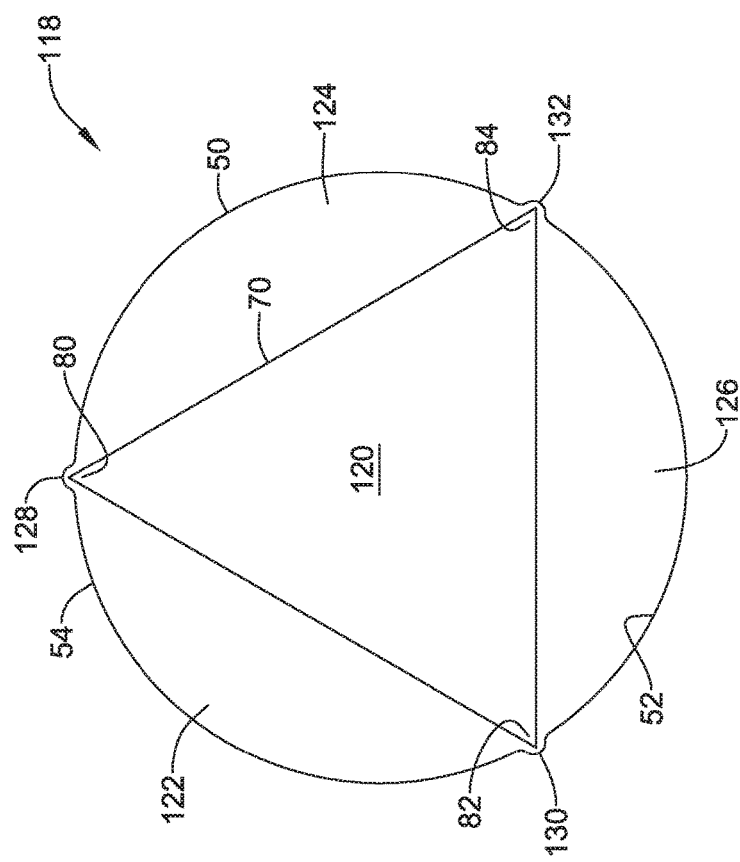
FIG. 7 is a cross-sectional view of a gastrointestinal assembly including the inner stent of FIG. 5 shown within the outer stent of FIG. 4.

FIG. 7 is a schematic cross-sectional view of an assembly 118 that includes the inner stent 70 (FIG. 5) disposed within the outer stent 50 (FIG. 4), such that the outer stent 50 circumscribers the inner stent 70, with the apices or corners of the inner stent 70 located at the circumference of the outer stent 50. It can be seen that the assembly 118 forms a nutritional content pathway 120 through the lumen of the inner stent 70 and a total of three drainage pathways 122, 124 and 126 defined between the outer surface of the inner stent 70 and the inner surface of the outer stent 50. As will be discussed and illustrated in subsequent drawings, when the assembly 118 has been deployed within the gastrointestinal tract 40 (FIG. 3), one or more of the drainage pathways 122, 124, 126 may be used to provide space for one or more drainage catheters, for example. In some cases, as illustrated, when expanded within the outer stent 50, the corners 80, 82, 84 of the triangular cross-sectional profile engage with the inner surface 52 of the outer stent 50 and in some instances when the inner stent 70 is expanded within the outer stent 50, the outward radial force applied to the outer stent 50 by the corners 80, 82, 84 of the inner stent 70 actually deforms the outer stent 50 such that anchoring protrusions 128, 130 and 132, corresponding to the corners 80, 82, 84, respectively, form in the outer surface 54 of the outer stent 50. The anchoring protrusions 128, 130, 132 may project radially outward from the circumference of the remainder of outer stent 50. In some embodiments, the anchoring protrusions 128, 130, 132 help to secure the assembly 118 in place within the gastrointestinal tract 40.

Figure 8:
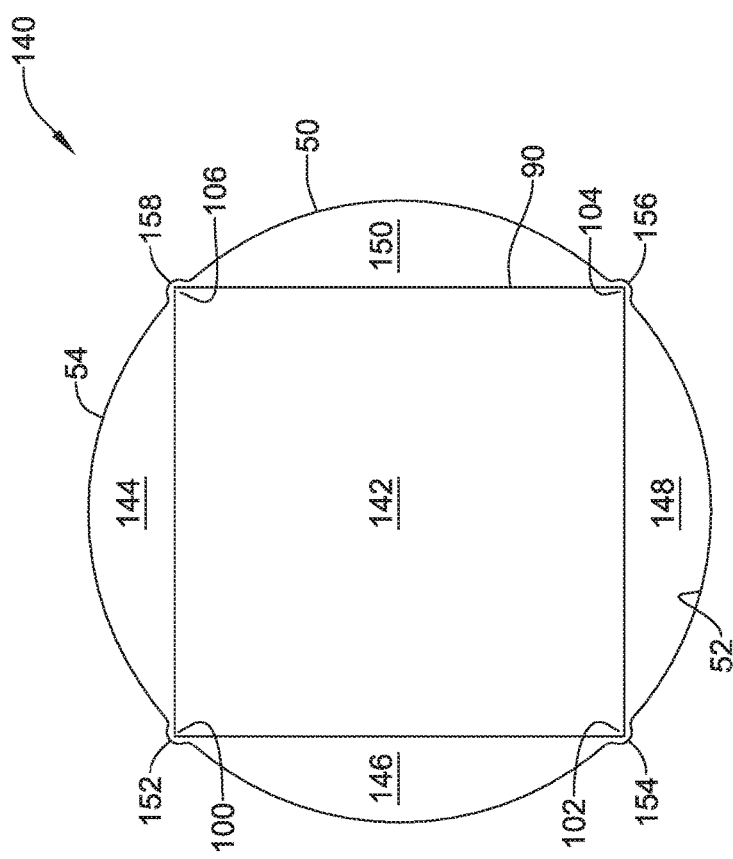
FIG. 8 is a cross-sectional view of a gastrointestinal assembly including the inner stent of FIG. 6 shown within the outer stent of FIG. 4.

FIG. 8 is a schematic cross-sectional view of an assembly 140 that includes the inner stent 90 (FIG. 6) disposed within the outer stent 50 (FIG. 4), such that the outer stent 50 circumscribers the inner stent 90, with the apices or corners of the inner stent 90 located at the circumference of the outer stent 50. It can be seen that the assembly 140 forms a nutritional content pathway 142 through the lumen of the inner stent 90 and a total of four drainage pathways 144, 146, 148 and 150 defined between the outer surface of the inner stent 90 and the inner surface of the outer stent 50. As will be discussed and illustrated in subsequent drawings, when the assembly 140 has been deployed within the gastrointestinal tract 40 (FIG. 3), one or more of the drainage pathways 144, 146, 148, 150 may be used to provide space for one or more drainage catheters, for example. In some cases, as illustrated, when expanded within the outer stent 50, the corners 100, 102, 104, 106 of the rectilinear cross-sectional profile engage with the inner surface 52 of the outer stent 50 and in some instances when the inner stent 90 is expanded within the outer stent 50, the outward radial force applied to the outer stent 50 by the corners 100, 102, 104, 106 of the inner stent 90 actually deforms the outer stent 50 such that anchoring protrusions 152, 154, 156 and 158, corresponding to the corners 100, 102, 104, 106, respectively, form in the outer surface 54 of the outer stent 50. The anchoring protrusions 152, 154, 156 and 158 may project radially outward from the circumference of the remainder of outer stent 50. In some embodiments, the anchoring protrusions 152, 154, 156, 158 help to secure the assembly 140 in place within the gastrointestinal tract 40.

Figure 9:
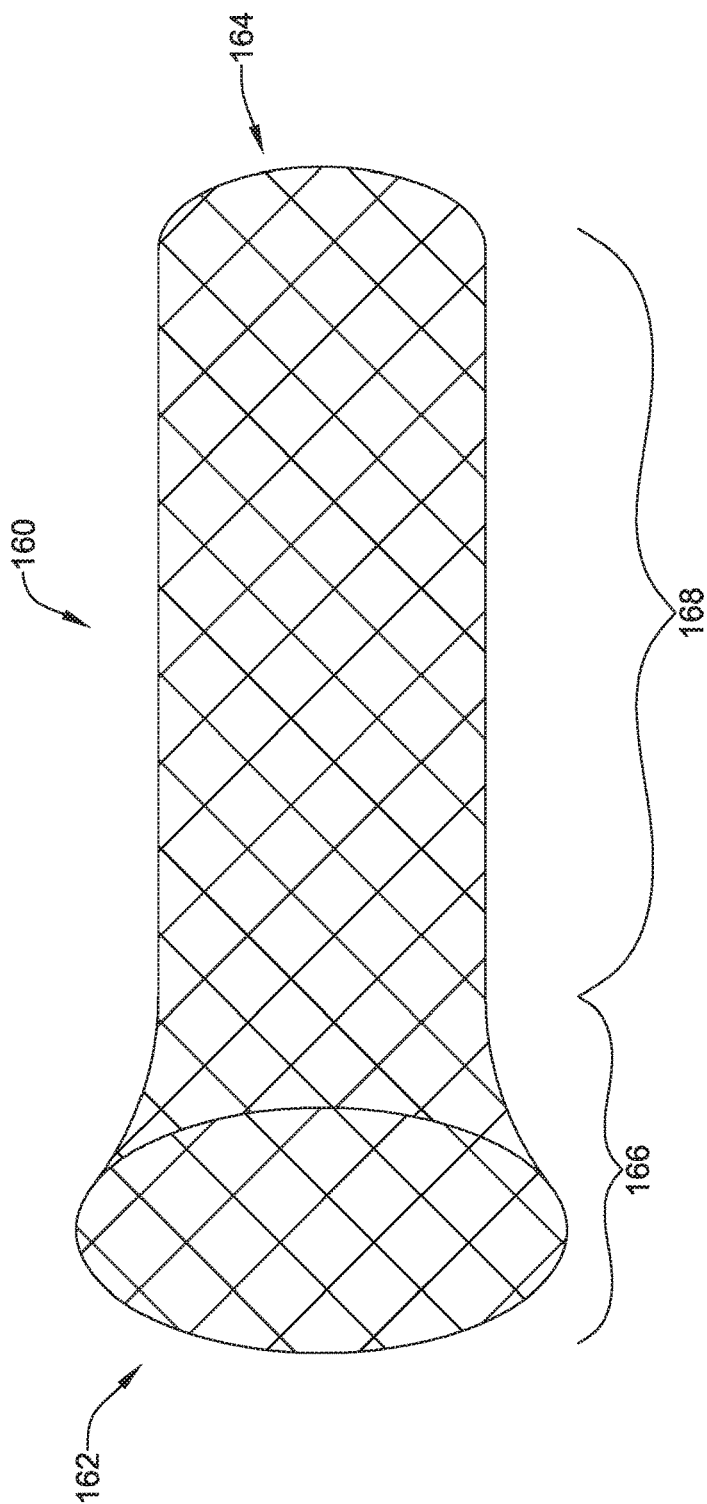
FIG. 9 is a schematic view of an inner stent in accordance with an embodiment of the disclosure.

In some cases, the inner stent, such as the inner stent 70 or the inner stent 90, may be configured to seal off an upper or proximal end of the drainage pathways 122, 124, 126 (FIG. 7) or the drainage pathways 144, 146, 148, 150 (FIG. 8) in order to keep nutritional contents out of the drainage pathways and thus away from any drainage catheters deployed therein. FIG. 9 is a schematic view of an inner stent 160 extending from a proximal end 162 to a distal end 164. In some cases, the inner stent 160 may be considered as representing an alteration to the inner stent 70 (FIG. 5) having a triangular cross-sectional profile or to the inner stent 90 (FIG. 6) having a rectilinear cross-sectional profile. The inner stent 160 includes a flared upper or proximal portion 166 and a non-cylindrical lower or distal portion 168. The flared upper or proximal portion 166 may be considered as transitioning from a non-circular cross-sectional profile of the non-cylindrical lower or distal portion 168 (such as a polygonal cross-sectional profile) to a circular cross-sectional profile of the flared upper or proximal portion 166.

Figure 10:
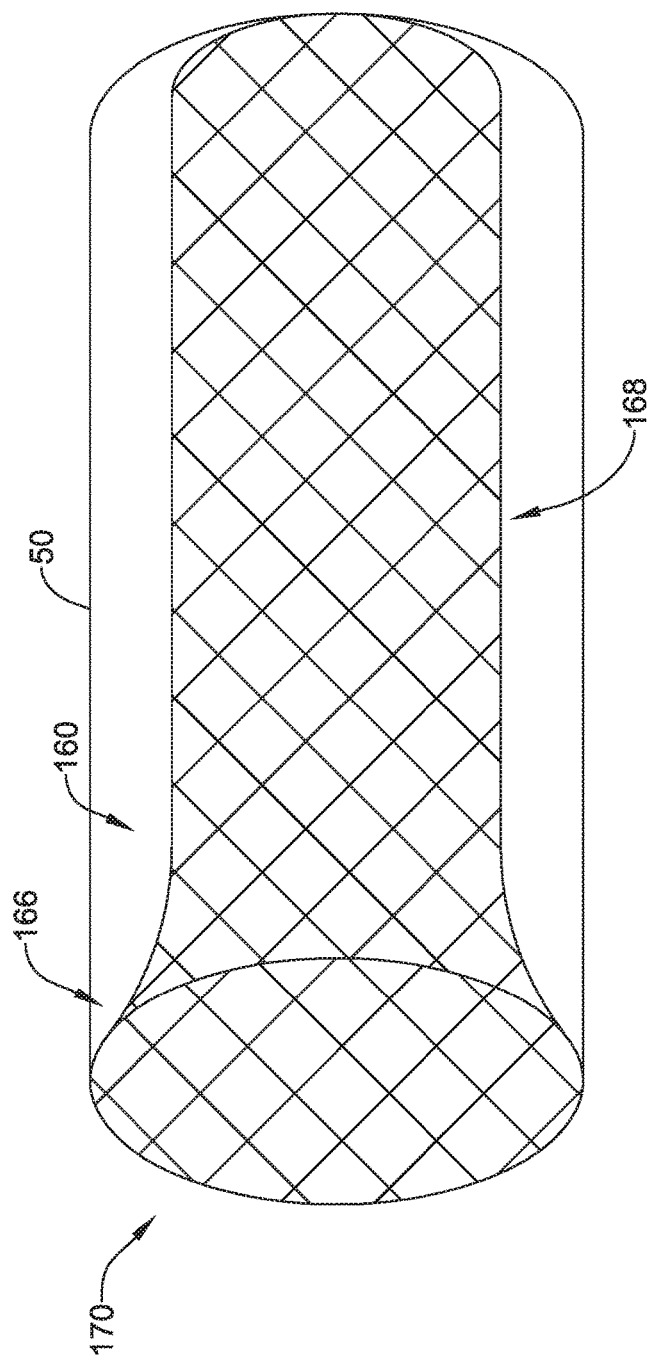
FIG. 10 is a schematic view of the inner stent of FIG. 9 shown within the outer stent of FIG. 4.

As can be seen in FIG. 10, which shows an assembly 170 including the inner stent 160 disposed within the outer stent 50, the flared upper or proximal portion 166 may be sized and configured to engage the inner surface 52 of the outer stent 50 around the entire circumference or substantially the entire circumference of the outer stent 50 and/or may be sized and configured to engage the proximal end of the outer stent 50 around the entire circumference or substantially the entire circumference of the outer stent 50, closing off the proximal end of the drainage pathways and funneling or directing nutritional contents through the lumen of the inner stent 160. As shown in FIG. 10, the flared upper or proximal portion 166 may extend distally into the lumen of the outer stent 50, transitioning into the non-cylindrical lower or distal portion 168 within the outer stent 50. The lower or distal portion 168 of the inner stent 160 may extend to or substantially to the distal end of the outer stent 50. However, in some instances, the distal portion 168 of the inner stent 160 may be located proximal of the distal end of the outer stent 50 or distal of the distal end of the outer stent 50, if desired.

The non-cylindrical lower or distal portion 168 may have a polygonal cross-sectional profile such as described above. For example, the lower or distal portion may have a triangular cross-sectional profile similar to the inner stent 70 (FIG. 5) or a rectilinear cross-sectional profile similar to the inner stent 90 (FIG. 6), although other configurations are contemplated. The non-cylindrical lower or distal portion 168 may have three or more sides, such as straight sides, converging at three or more apices or corners, for example. The outer stent 50 may circumscribe the inner stent 90, and in some cases, the apices or corners of the lower or distal portion 168 of the inner stent 160 may be positioned at the circumference of the outer stent 50. Similar to the embodiments described above, in some cases when expanded within the outer stent 50, the corners of the cross-sectional profile of the lower or distal portion 168 of the inner stent 160 may engage with the inner surface of the outer stent 50 and in some instances when the inner stent 160 is expanded within the outer stent 50, the outward radial force applied to the outer stent 50 by the corners of the lower or distal portion 168 of the inner stent 160 actually deforms the outer stent 50 such that anchoring protrusions, similar to that described above, corresponding to the corners of the lower or distal portion 168 of the inner stent 160 form in the outer surface of the outer stent 50. The anchoring protrusions may project radially outward from the circumference of the remainder of outer stent 50. In some embodiments, the anchoring protrusions help to secure the assembly 170 in place within the gastrointestinal tract 40.

In other instances, the lower or distal portion 168 of the inner stent 160 may be cylindrical, having a diameter less than the diameter of the outer stent 50, providing an annular drainage pathway between the inner surface of the outer stent 50 and the outer surface of the lower or distal portion 168 of the inner stent 160.

In some cases the inner stent 160 and/or the outer stent 50 may, for example, be a braided stent, a woven stent or a laser-cut stent. In some cases, the inner stent 160 may include a polymeric covering or coating extending over at least part of, or the entire expandable framework of the inner stent 160, forming a fully or partially covered stent. For example, the upper or proximal portion 166 and/or the lower or distal portion 168 may be covered with a polymeric covering or coating. In some cases, the outer stent 50 may include a polymeric covering or coating extending over at least part of, or the entire expandable framework of the outer stent 50, forming a fully or partially covered stent. In some instances, the inner stent 160 and/or the outer stent 50 may not include the polymeric covering or coating.

Figure 11:
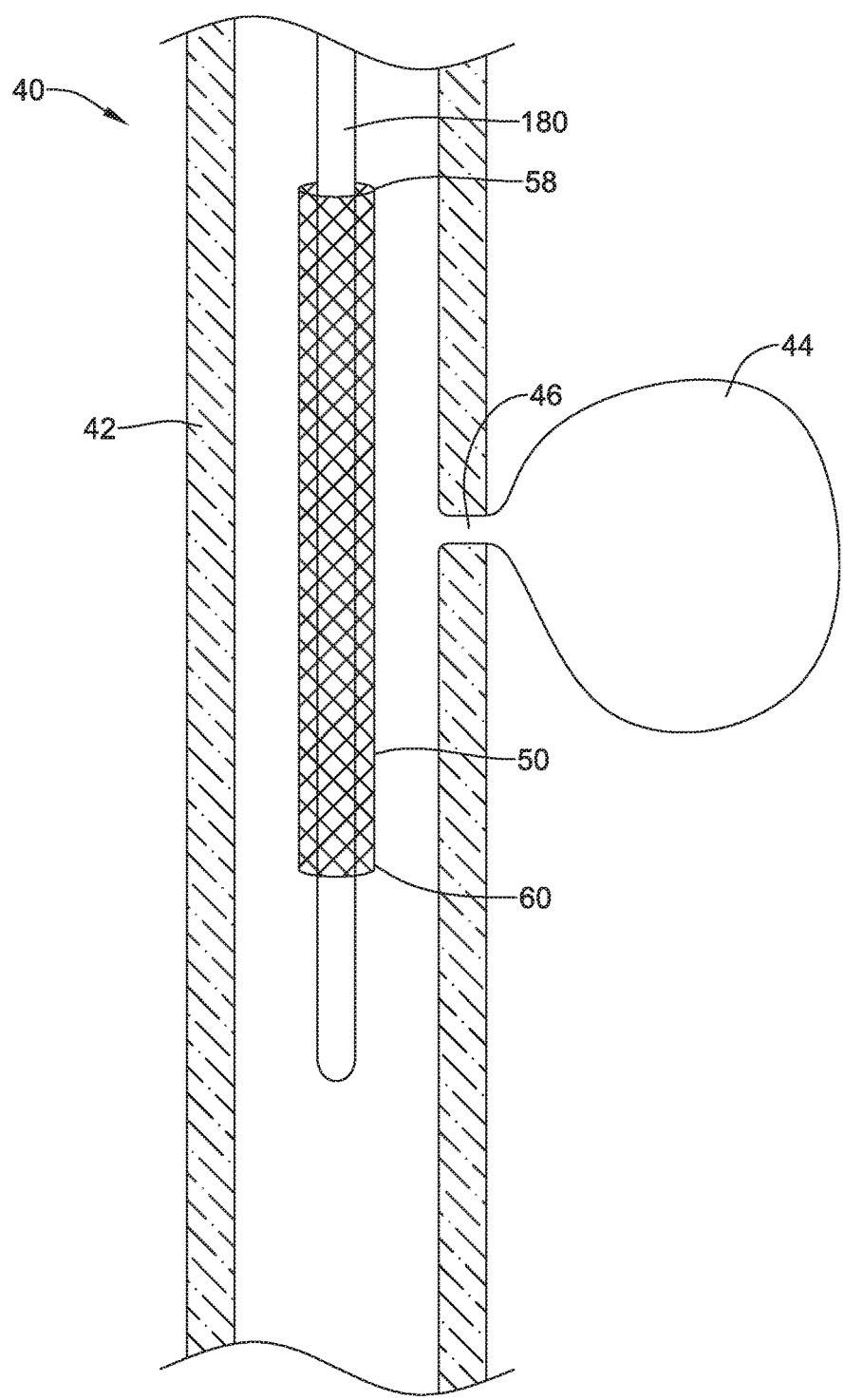
FIGS. 11 through 15 illustrate a method of deploying a gastrointestinal assembly within a patient's gastrointestinal tract in accordance with an embodiment of the disclosure.
Figure 12:
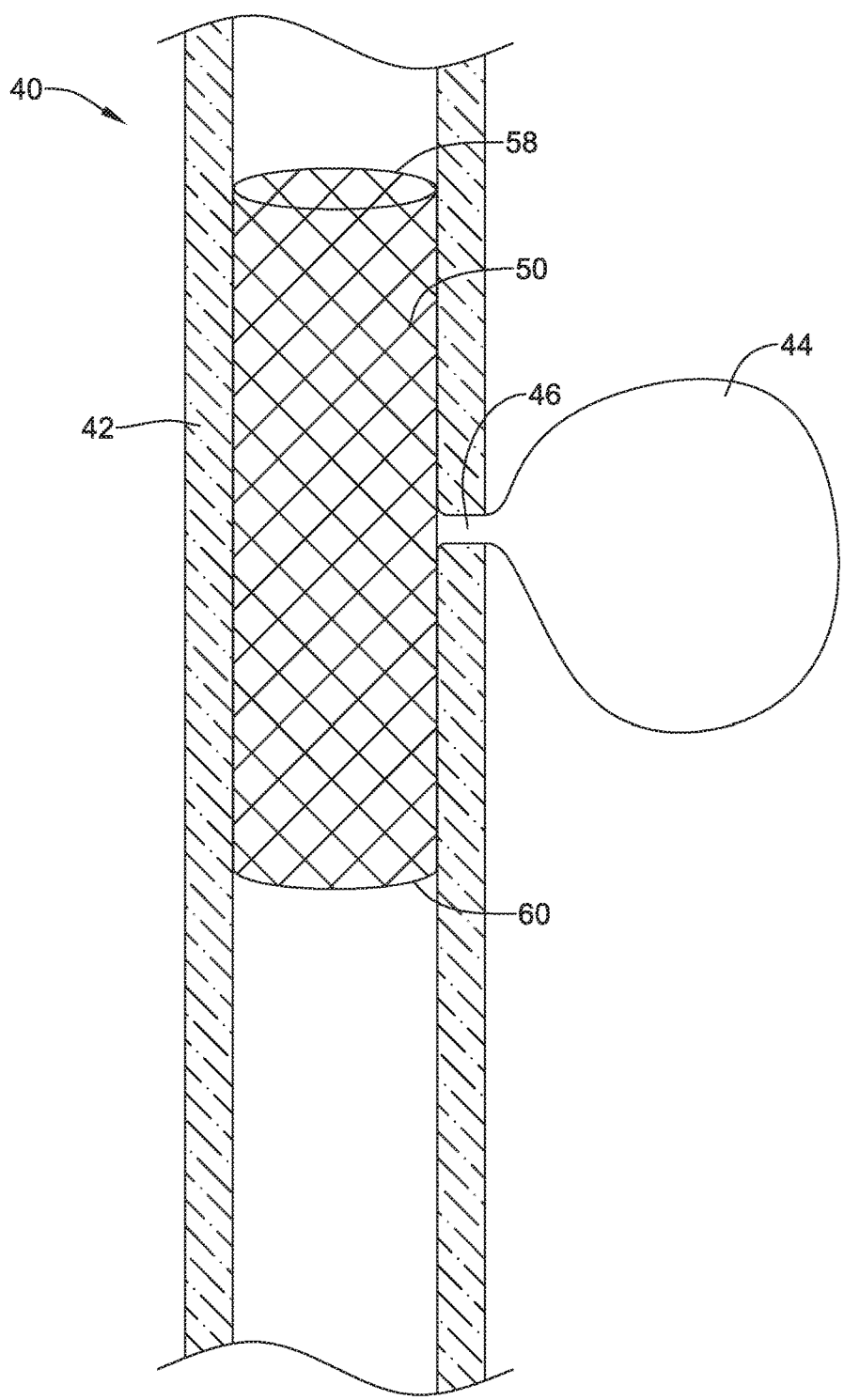

FIGS. 11 through 15 provide an illustrative but non-limiting example of a method of deploying a gastrointestinal assembly within the gastrointestinal tract 40. As will be illustrated, in some instances, the gastrointestinal assembly is deployed piece by piece. In FIG. 11, the outer stent 50 is in its compressed configuration for delivery, and is disposed on a schematically-illustrated delivery catheter 180. The delivery catheter 180 has been advanced until the outer stent 50 is positioned adjacent the fistula 46 of the abscess 44. The outer stent 50 may then be expanded into its expanded configuration against the wall 42 of the gastrointestinal tract 40 and the delivery catheter 180 may then be removed, as shown for example in FIG. 12. In the expanded configuration, the outer stent 50 may be positioned across the fistula 46, with a proximal portion of the outer stent 50 positioned proximal of the fistula 46 and a distal portion of the outer stent 50 positioned distal of the fistula 46.

The outer stent 50 may be self-expanding or balloon-expandable. In situations where the outer stent 50 is self-expanding, the delivery catheter 180 may for example include a retractable sheath (not illustrated) that may cover the outer stent 50 for advancement to a desired position within the gastrointestinal tract 40. Once the desired position has been reached, the outer stent 50 may for example be expanded into its expanded configuration against the wall 42 of the gastrointestinal tract 40 simply by retracting the sheath. In some cases, in its expanded configuration, the outer stent 50 may be considered as making substantial contact with the gastrointestinal tract 40. In other instances, the delivery catheter 180 may include an inflatable balloon or other expandable member positioned within the outer stent 50 that may be expanded radially outward to expand the outer stent 50 into its expanded configuration against the wall 42 of the gastrointestinal tract 40.

Figure 13:
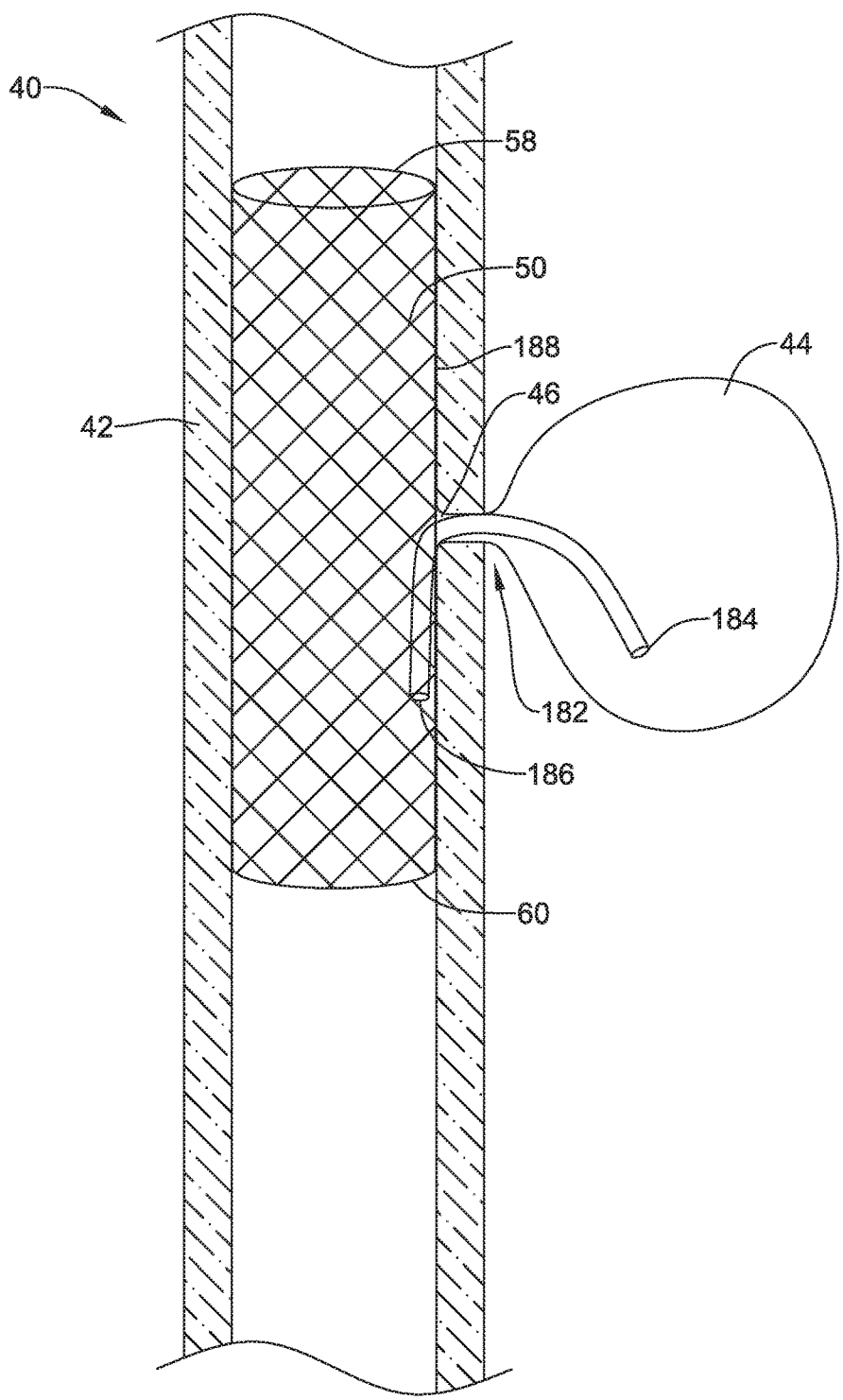

A drainage catheter 182 having a first end 184 and a second end 186 may be deployed as shown for example in FIG. 13. The first end 184 of the drainage catheter 182 may be extended through a side wall 188 of the outer stent 50, through the fistula 46 and into the abscess 44. In some instances, the second end 186 of the drainage catheter 182 may be positioned in the lumen of the outer stent 50. However, in some cases, the drainage catheter 182 may have a length sufficient to permit the drainage catheter 182 to extend through the lumen of the outer stent 50 from the abscess 44 such that the second end 186 of the drainage catheter 182 extends distally to the distal end of the outer stent 50 and/or distally beyond the distal end of the outer stent 50. In some cases, the drainage catheter 182 may instead extend exterior to the outer stent 50.

While a single drainage catheter 182 is illustrated, it will be appreciated that in some cases, it may be desirable to add two or more drainage catheters 182 to facilitate drainage of the abscess 44. In some cases, there may be several distinct abscesses 44, or a single abscess 44 may have more than one fistula 46. Once the drainage catheter(s) 182 has/have been placed, the inner stent 70 may be deployed to form the aforementioned nutritional content pathway and drainage pathways.

Figure 14:
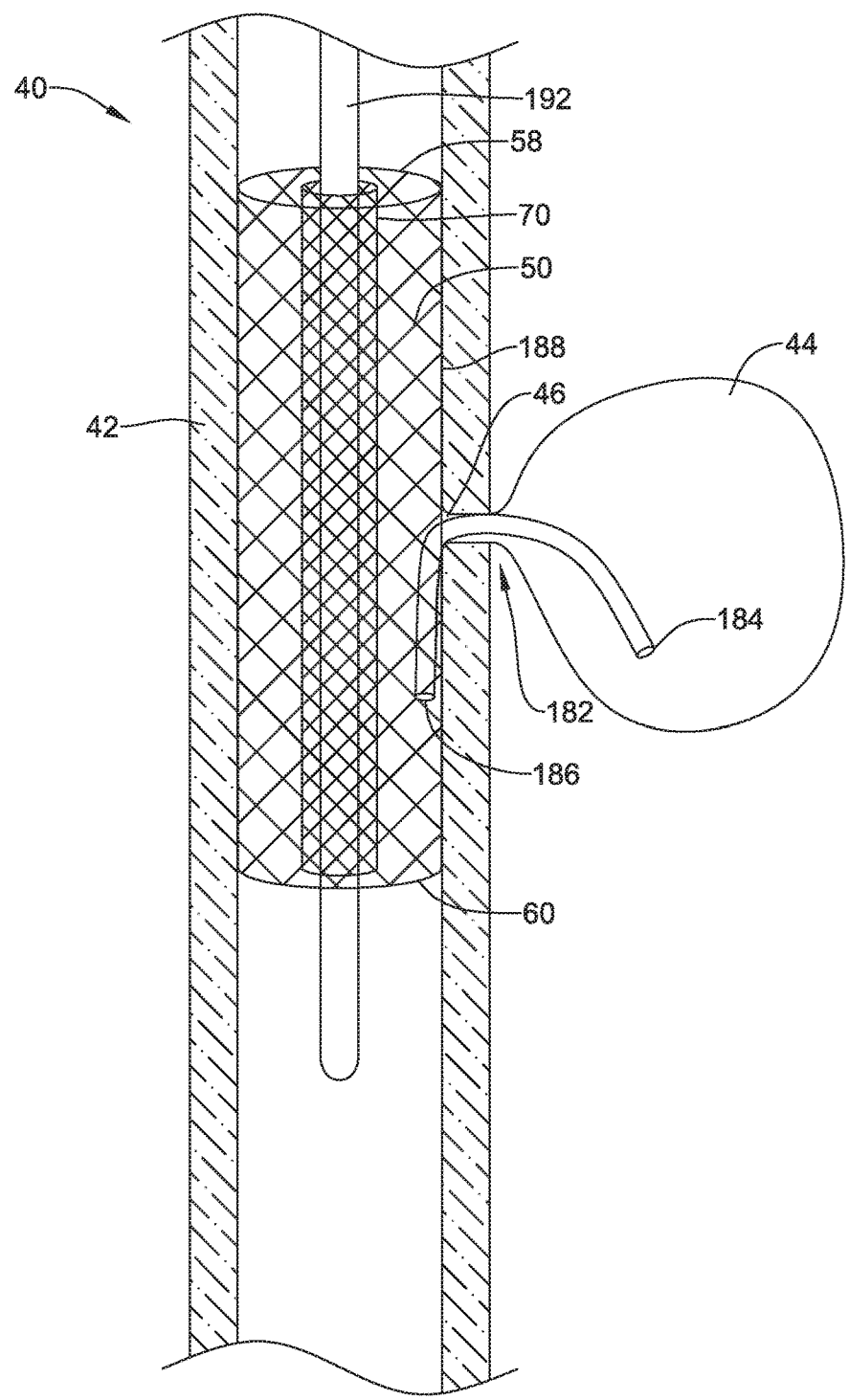
Figure 15:
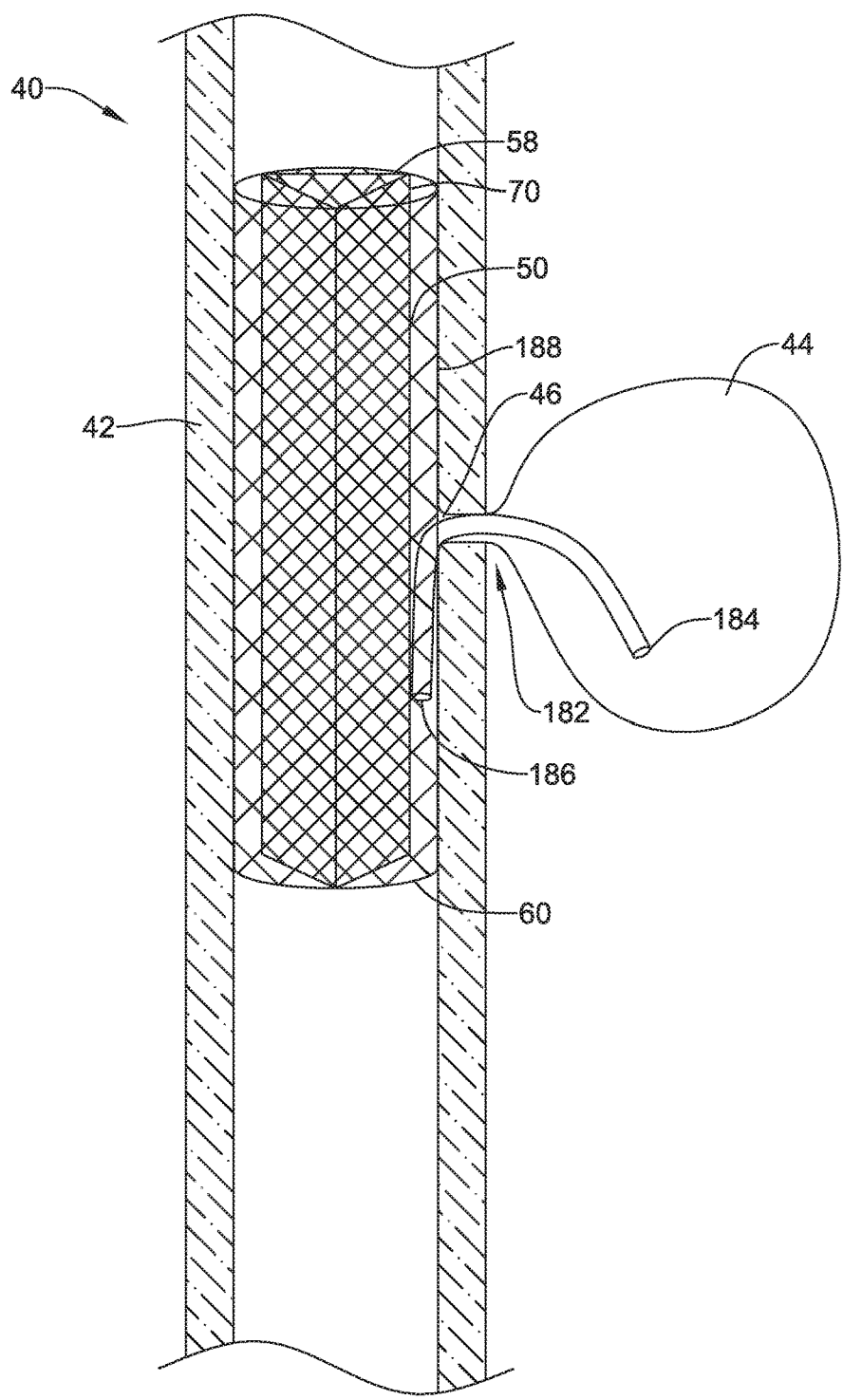

In FIG. 14, the inner stent 70 is in its compressed configuration for delivery, and is disposed on a schematically-illustrated delivery catheter 192. The delivery catheter 192 has been advanced until the inner stent 70 is positioned within the expanded outer stent 50. It will be appreciated that showing the inner stent 70 is merely illustrative, as the inner stent 90 or another inner stent having another non-cylindrical profile could also be used. The inner stent 70 may then be expanded into its expanded configuration and the delivery catheter 192 may then be removed, as shown for example in FIG. 15. The inner stent 70 may be self-expanding, for example. Accordingly, the delivery catheter 192 may for example include a retractable sheath (not illustrated) that may cover the inner stent 70 for advancement to a desired position within the gastrointestinal tract 40. Once the desired position has been reached, the inner stent 70 may for example be expanded into its expanded configuration simply by retracting the sheath. Alternatively, the inner stent 70 may be expanded radially outward into its expanded configuration with an inflatable balloon or other expandable member positioned within the inner stent 70.

When the inner stent 70, which may be a fully covered stent including a covering extending over the expandable framework, is expanded within the outer stent 50, the corners of the cross-sectional profile of the inner stent 70 may engage with the inner surface of the outer stent 50 forming a plurality of discrete drainage pathways defined between the outer surface of the inner stent 70 and the inner surface of the outer stent 50 and a nutritional content pathway through the lumen of the inner stent 70. The drainage catheter 182 may be positioned in one of the drainage pathways defined between the inner stent 70 and the outer stent 50. Thus, the inner stent 70 may isolate the drainage catheter 182 from the inner lumen of the inner stent 70 and thus from the nutritional content pathway through the assembly.

In some instances when the inner stent 70 is expanded within the outer stent 50, the outward radial force applied to the outer stent 50 by the corners of the inner stent 70 actually deforms the outer stent 50 such that anchoring protrusions, similar to that described above, corresponding to the corners of the inner stent 70 form in the outer surface of the outer stent 50. The anchoring protrusions may project radially outward from the circumference of the remainder of outer stent 50 into the wall 42 of the gastrointestinal tract 40 to help secure the assembly in place within the gastrointestinal tract 40.

Figure 16:
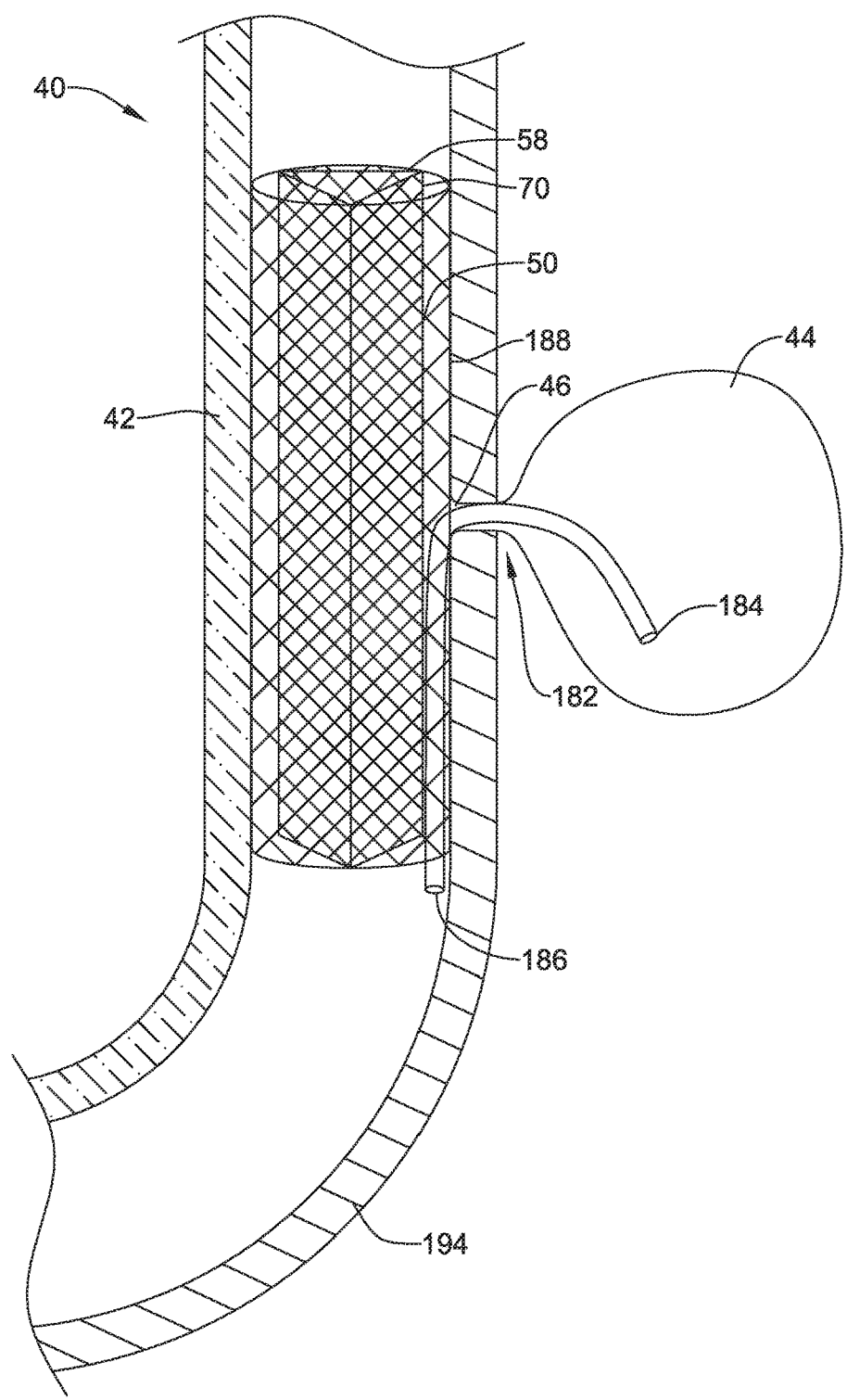
FIG. 16 is a schematic view of a gastrointestinal assembly deployed within a patient's gastrointestinal tract in accordance with an embodiment of the disclosure.

FIG. 16 provides a schematic view of a gastrointestinal assembly, such as a gastrointestinal drainage assembly, that combines the inner stent 70 and the outer stent 50 within the gastrointestinal tract 40. It will be appreciated that the flared upper portion of the inner stent 70 is not shown in this view. However, it is contemplated that the inner stent 70 may include a flared upper or proximal portion closing off the proximal end of the drainage pathways between the inner stent 70 and the outer stent 50 in order to funnel or direct nutritional contents through the lumen of the inner stent 70 while isolating the drainage catheter 182 from nutritional contents passing through the gastrointestinal tract 40 through the lumen of the inner stent 70. In FIG. 16, the outer stent 50 is shown in phantom, exposing the inner stent 70 to view. It can be seen that in FIG. 16, one of the side walls 42 of the gastrointestinal tract 40 can be seen as including a staple line 194, such as the staple lines 20, 22 (FIG. 1) or the staple lines 30, 32 (FIG. 2). In some instances, as illustrated, the second end 186 of the drainage catheter 182 may have a length sufficient to permit the drainage catheter 182 to extend through the lumen of the outer stent 50 from the abscess 44 such that the second end 186 of the drainage catheter 182 extends distally to the distal end of the outer stent 50 and/or distally beyond the distal end of the outer stent 50.

In some cases, the gastrointestinal assembly shown in FIG. 16 may permit the abscess 44 to drain via the drainage catheter 182 without nutritional contents such as food and beverages interfering with the drainage process as nutritional contents may pass through an interior of the inner stent 70. The drainage catheter 182 may be disposed within a drainage pathway (such as the drainage pathways 122, 124, 126 (FIG. 7) or the drainage pathways 144, 146, 148, 150 (FIG. 8). As a result, the abscess 44 can drain without nutritional contents getting in the way or otherwise interfering with the drainage catheter 182. In some cases, protecting the abscess 44 from nutritional contents, and stomach acid, may facilitate healing of the abscess 44.

It will be appreciated that a variety of different materials may be used in forming the stents 50, 70, 90 and 160. In some embodiments, for example, the polymeric covering 64, 110, 112 may include any suitable polymeric material, including biocompatible materials such as polyurethane or silicone. Other suitable polymers include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

The expandable framework forming the stents 50, 70, 90, 160 may be formed of any suitable desired material, such as a biocompatible material including biostable, bioabsorbable, biodegradable or bioerodible materials. For instance, the expandable framework may be formed of a polymeric material or a metallic material. Some suitable polymeric materials are listed above. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof.

In some embodiments, the expandable framework may include one or more metals. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In some embodiments, the stents 50, 70, 90, 160 may be coated with or otherwise include an elutable drug. The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific drugs or therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well as derivatives of the forgoing, among many others.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A gastrointestinal assembly for facilitating drainage of an abscess, the gastrointestinal assembly configured to be deployed within a patient's gastrointestinal tract proximate the abscess, the gastrointestinal assembly comprising:
an outer stent having an expanded configuration in which an outer surface of the outer stent engages the patient's gastrointestinal tract, the outer stent having an inner surface defining a volume within the outer stent; an inner stent disposed within the outer stent, the inner stent having an expanded configuration in which the inner stent divides the volume into a primary passageway through which nutritional contents may pass and a secondary passageway protected from nutritional contents and configured to accommodate a passive drainage system for draining the abscess; and wherein the outer stent has a cylindrical profile and the inner stent has a non-cylindrical lower portion defining the secondary passageway between the inner stent and the outer stent, and the inner stent has a flared upper portion that is configured to seal against the cylindrical profile of the outer stent.

2. The gastrointestinal assembly of claim 1, wherein the inner stent comprises:
an expandable framework defining the non-cylindrical portion and the flared upper portion; and
a polymeric covering disposed over at least part of the expandable framework.

3. The gastrointestinal assembly of claim 1, wherein the non-cylindrical lower portion of the inner stent has a polygonal cross-sectional profile.

4. The gastrointestinal assembly of claim 1, wherein the non-cylindrical lower portion of the inner stent has a triangular cross-sectional profile.

5. The gastrointestinal assembly of claim 1, wherein the non-cylindrical lower portion of the inner stent has a rectilinear cross-sectional profile.

6. The gastrointestinal assembly of claim 1, further comprising a drainage catheter having a first portion extending through a fistula of the abscess and into the abscess, the drainage catheter having a second portion extending downwardly from the abscess through the secondary passageway.

7. The gastrointestinal assembly of claim 6, wherein the drainage catheter extends through a wall of the outer stent.

8. A gastrointestinal drainage assembly for facilitating drainage of an abscess, the gastrointestinal assembly configured to be deployed within a patient's gastrointestinal tract proximate the abscess, the gastrointestinal assembly comprising:
an outer expandable framework configured to engage the patient's gastrointestinal tract when in its expanded configuration;
the outer expandable framework having a cylindrical profile;
an inner expandable framework disposed within the outer expandable framework and in contact with the outer expandable framework when the inner expandable framework is in its expanded configuration;
the inner expandable framework having a non-cylindrical lower portion that defines a nutritional content pathway through the inner expandable framework and one or more drainage pathways disposed between the inner expandable framework and the outer expandable framework;
the inner expandable framework having a flared upper portion that engages the outer expandable framework and seals off an upper end of the one or more drainage pathways.

9. The gastrointestinal drainage assembly of claim 8, further comprising a drainage catheter having a first portion extending into the abscess and a second portion extending downwardly from the abscess through the one of the one or more drainage pathways.

10. The gastrointestinal drainage assembly of claim 8, wherein the inner expandable framework contacts the outer expandable framework along one or more contact lines, and the inner expandable framework deforms the outer expandable framework in an outward direction along the one or more contact lines in order to anchor the gastrointestinal drainage assembly in position within the gastrointestinal tract.

11. The gastrointestinal drainage assembly of claim 8, further comprising a polymeric covering disposed over at least a portion of the inner expandable framework.

12. The gastrointestinal drainage assembly of claim 8, further comprising a polymeric covering disposed over at least a portion of the outer expandable framework.

13. The gastrointestinal drainage assembly of claim 8, wherein the non-cylindrical lower portion of the inner expandable framework has a polygonal cross-sectional profile.

14. The gastrointestinal drainage assembly of claim 8, wherein the non-cylindrical lower portion of the inner expandable framework has a triangular cross-sectional profile.

15. The gastrointestinal drainage assembly of claim 8, wherein the non-cylindrical lower portion of the inner expandable framework has a rectilinear cross-sectional profile.

16. A method of facilitating drainage of an abscess proximate a patient's gastrointestinal tract, the method comprising:

advancing an outer stent into position proximate the abscess and expanding the outer stent such that the outer stent makes substantial contact with the gastrointestinal tract;

extending a first end of a drainage catheter through a side wall of the outer stent and into the abscess, the drainage catheter having a length sufficient to permit a second end of the drainage catheter to extend distally from the abscess;

advancing an inner stent into the expanded outer stent and expanding the inner stent, the expanded inner stent defining a primary passageway through which nutritional contents may pass and a secondary passageway through which the drainage catheter extends;

the inner stent having a flared proximal end that seals the proximal end of the secondary passageway to keep nutritional contents out of the secondary passageway.

17. The method of claim 16, wherein the outer stent has a cylindrical profile when expanded and the inner stent, when expanded, has a non-cylindrical lower portion defining the secondary passageway between the inner stent and the outer stent.

18. The method of claim 16, wherein expanding the inner stent causes the inner stent to contact the outer stent along one or more contact lines, and the inner stent deforms the outer stent in an outward direction along the one or more contact lines in order to anchor the gastrointestinal drainage assembly in position within the gastrointestinal tract.

19. The method of claim 16, further comprising a subsequent step of removing the inner stent, the outer stent and the drainage catheter once the abscess has healed.

* * * * *